United States Patent
Suzuki

(10) Patent No.: US 12,185,916 B2
(45) Date of Patent: Jan. 7, 2025

(54) ENDOSCOPE APPARATUS, PROCESSOR FOR ENDOSCOPE IMAGE, AND METHOD FOR GENERATING ENDOSCOPE IMAGE

(71) Applicant: OLYMPUS CORPORATION, Tokyo (JP)

(72) Inventor: Takeo Suzuki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 44 days.

(21) Appl. No.: 17/900,135

(22) Filed: Aug. 31, 2022

(65) Prior Publication Data
US 2022/0409011 A1   Dec. 29, 2022

Related U.S. Application Data

(63) Continuation of application No. PCT/JP2020/009821, filed on Mar. 6, 2020.

(51) Int. Cl.
*A61B 1/00* (2006.01)
*G02B 23/24* (2006.01)

(52) U.S. Cl.
CPC ...... *A61B 1/00193* (2013.01); *A61B 1/00009* (2013.01); *A61B 1/00096* (2013.01);
(Continued)

(58) Field of Classification Search
CPC ............ A61B 1/00193; A61B 1/00186; A61B 1/00177; A61B 1/00179; A61B 1/00174
See application file for complete search history.

(56) References Cited

U.S. PATENT DOCUMENTS

| 2002/0068853 A1* | 6/2002 | Adler ................. | A61B 1/00082 600/109 |
| 2010/0208046 A1* | 8/2010 | Takahashi .......... | G02B 23/2415 348/E7.085 |

(Continued)

FOREIGN PATENT DOCUMENTS

| EP | 3 145 176 A1 | 3/2017 |
| JP | H09-5643 A | 1/1997 |

(Continued)

OTHER PUBLICATIONS

EPO, partial Machine Translation of JP2014228851A (Year: 2014).*

(Continued)

*Primary Examiner* — David N Werner
(74) *Attorney, Agent, or Firm* — Scully, Scott, Murphy & Presser, P.C.

(57) ABSTRACT

An endoscope apparatus includes first and second optical lenses that are separately provided at a distal end portion of an endoscope, and form first and second optical images, respectively, an optical path length changing filter that makes optical path lengths of the first and second optical images different, an image pickup device that performs image pickup of the first and second optical images to generate first and second image pickup signals, and a processor that generates first and second images from the first and second image pickup signals, corrects parallax, removes an area including a figure present only in one of the first and second images, and combines respective focusing areas of the first and second images to generate an endoscope image.

19 Claims, 6 Drawing Sheets

(52) U.S. Cl.
CPC ...... *A61B 1/00174* (2013.01); *A61B 1/00186* (2013.01); *A61B 1/00194* (2022.02); *G02B 23/2415* (2013.01)

(56) References Cited

U.S. PATENT DOCUMENTS

| | | | |
|---|---|---|---|
| 2014/0066704 A1* | 3/2014 | Blumenkranz | A61B 1/0005 600/114 |
| 2014/0267626 A1* | 9/2014 | Lilagan | A61B 1/00193 348/46 |
| 2014/0302452 A1* | 10/2014 | Hack | A61B 1/00193 433/29 |
| 2017/0049306 A1* | 2/2017 | Katakura | A61B 1/00096 |
| 2017/0086649 A1 | 3/2017 | Mizuno | |
| 2017/0086679 A1 | 3/2017 | Sekiya et al. | |
| 2017/0230634 A1 | 8/2017 | Takenouchi et al. | |
| 2018/0042453 A1* | 2/2018 | Hino | G02B 23/2415 |
| 2019/0302444 A1* | 10/2019 | Yokohama | A61B 1/00193 |
| 2019/0376784 A1* | 12/2019 | Tewes | A61B 1/00194 |
| 2020/0060550 A1* | 2/2020 | Pesach | A61C 19/04 |
| 2020/0082529 A1* | 3/2020 | Mikami | G06T 7/70 |
| 2020/0345215 A1* | 11/2020 | Springer | A61B 1/00193 |
| 2022/0272315 A1* | 8/2022 | Voss | A61B 1/24 |

FOREIGN PATENT DOCUMENTS

| | | |
|---|---|---|
| JP | 2009-240531 A | 10/2009 |
| JP | 2012-095828 A | 5/2012 |
| JP | 5593004 B2 | 9/2014 |
| JP | 2014-228851 A | 12/2014 |
| WO | 2014/002740 A1 | 1/2014 |
| WO | 2016/059983 A1 | 4/2016 |
| WO | 2016/072490 A1 | 5/2016 |

OTHER PUBLICATIONS

WIPO, International Preliminary Report on Patentability for PCT/JP2020/009821 (Year: 2022).*

International Search Report dated May 26, 2020 received in PCT/JP2020/009821.

* cited by examiner

ENDOSCOPE APPARATUS, PROCESSOR FOR ENDOSCOPE IMAGE, AND METHOD FOR GENERATING ENDOSCOPE IMAGE

CROSS REFERENCE TO RELATED APPLICATION

This application is a continuation application of PCT/JP2020/009821 filed on Mar. 6, 2020, the entire contents of which are incorporated herein by this reference.

BACKGROUND OF THE INVENTION

1. Field of the Invention

The present invention relates to an endoscope apparatus, a processor for endoscope image, and a method for generating an endoscope image in which a plurality of images having different optical path lengths are acquired to generate an extended depth-of-focus image.

2. Description of the Related Art

It is known that an optical image of a subject located at a position proximate to an optical lens has a shallow depth of focus. Thus, a dual-focus endoscope that can switch a focus position between a near point and a far point to perform observation has been conventionally proposed. A zoom endoscope that can magnify a subject for observation is also conventionally known.

However, such conventional endoscopes require a switching operation between the near point and the far point or a zoom operation. Therefore, an extended depth-of-focus endoscope has been proposed which enables the near point and the far point to be observed concurrently without requiring any operation. The extended depth-of-focus endoscope acquires a first image focused on the near point and a second image focused on the far point, and combines portions in focus in the images to generate an extended depth-of-focus image, for example.

For example, International Publication No. WO2014/002740 describes an endoscope system including an objective optical system, optical path division means for dividing a subject image entered from the objective optical system into two optical images with different focuses, an image pickup device that concurrently performs image pickup of the two optical images with different focuses to acquire two images, image correction means for correcting the two images such that differences other than the focuses become substantially the same, and an image combination processing unit that selects portions having a relatively high contrast in the corrected two images to generate a combined image. More specifically, a beam splitter having a plurality of prisms combined is employed as the optical path division means.

SUMMARY OF THE INVENTION

An endoscope apparatus according to an aspect of the present invention includes a first optical lens provided at a distal end portion of an insertion section of an endoscope, and configured to form a first optical image of a subject, a second optical lens provided at the distal end portion separately from the first optical lens, and configured to form a second optical image of the subject with parallax relative to the first optical image, an optical path length changing member configured to make an optical path length of the first optical image and an optical path length of the second optical image different, an image pickup device configured to perform image pickup of the first optical image to generate a first image pickup signal, and perform image pickup of the second optical image to generate a second image pickup signal, and a processor configured to generate a first image based on the first image pickup signal, generate a second image based on the second image pickup signal, subject at least one of the first image or the second image to image processing of correcting the parallax, extract a first focusing area from the first image, extract a second focusing area from the second image, and combine the first focusing area and the second focusing area to generate an endoscope image, in which the processor is configured to combine the first focusing area and the second focusing area after removing an area including a figure present only in one of the first image and the second image.

A processor for endoscope image according to an aspect of the present invention is configured to acquire a first image pickup signal and a second image pickup signal from an endoscope including a first optical lens provided at a distal end portion of an insertion section inserted into a subject, and configured to form a first optical image of the subject, a second optical lens provided at the distal end portion separately from the first optical lens, and configured to form a second optical image of the subject with parallax relative to the first optical image, an optical path length changing member configured to make an optical path length of the first optical image and an optical path length of the second optical image different, and an image pickup device configured to perform image pickup of the first optical image to generate the first image pickup signal, and perform image pickup of the second optical image to generate the second image pickup signal, the processor for endoscope image is configured to generate a first image based on the first image pickup signal, generate a second image based on the second image pickup signal, subject at least one of the first image or the second image to image processing of correcting the parallax, extract a first focusing area from the first image, extract a second focusing area from the second image, and combine the first focusing area and the second focusing area to generate an endoscope image, and the processor for endoscope image is configured to combine the first focusing area and the second focusing area after removing an area including a figure present only in one of the first image and the second image.

A method for generating an endoscope image according to an aspect of the present invention includes forming a first optical image of a subject by a first optical lens provided at a distal end portion of an insertion section of an endoscope, forming a second optical image of the subject with parallax relative to the first optical image by a second optical lens provided at the distal end portion separately from the first optical lens, making, by an optical path length changing member, an optical path length of the first optical image and an optical path length of the second optical image different, causing an image pickup device to perform image pickup of the first optical image to generate a first image pickup signal, and perform image pickup of the second optical image to generate a second image pickup signal, causing a processor to generate a first image based on the first image pickup signal, generate a second image based on the second image pickup signal, and subject at least one of the first image or the second image to image processing of correcting the parallax, causing the processor to remove an area including a figure present only in one of the first image and the second image, and causing the processor to extract a first focusing area from the first image, extract a second focusing area from the second image, and combine the first focusing area and the second focusing area to generate an endoscope image.

DETAILED DESCRIPTION OF THE PREFERRED EMBODIMENTS

Figure 1:
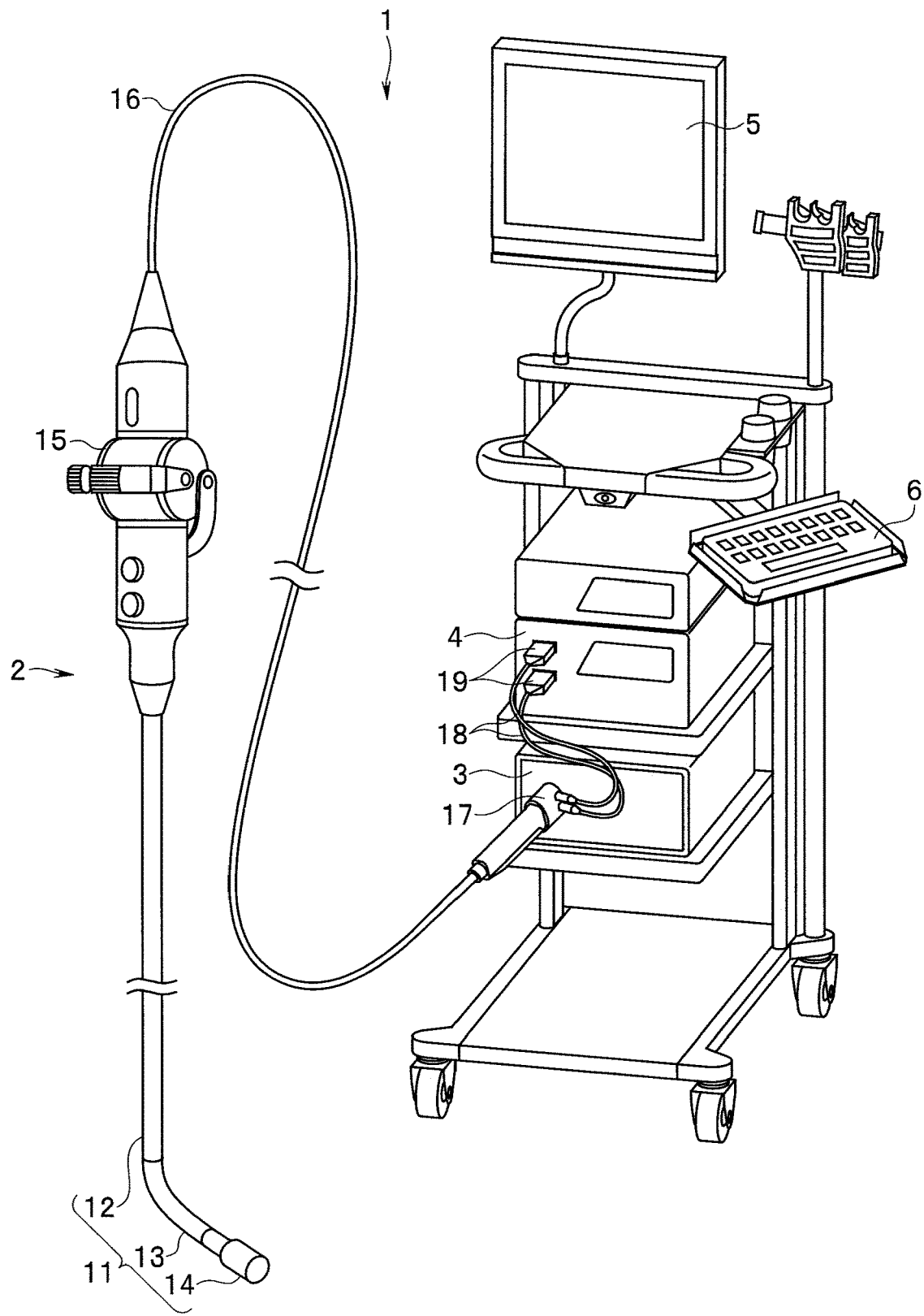
FIG. 1 is a perspective view showing a configuration example of an endoscope apparatus in a first embodiment of the present invention.

Hereinafter, embodiments of the present invention will be explained with reference to the drawings. However, the present invention is not limited by the embodiments which will be explained below.

Note that in the illustration of the drawings, the same or corresponding elements have the same reference characters allotted as appropriate. It should be noted that the drawings are schematic, and a dimensional relationship between respective elements, ratios of the respective elements, and the like in one of the drawings may differ from actual ones. Further, the plurality of drawings may include portions having dimensional relationships and ratios different from one another.

First Embodiment

FIG. 1 to FIG. 6 show a first embodiment of the present invention, and FIG. 1 is a perspective view showing a configuration example of an endoscope apparatus 1.

As shown in FIG. 1, the endoscope apparatus 1 of the present embodiment includes an endoscope 2, a light source device 3, a processor 4, a monitor 5, and a keyboard 6.

Note that although the following will be explained using a case in which the endoscope 2 is a flexible endoscope as an example, the endoscope 2 may be a rigid endoscope. Although the following will be explained using a case in which the endoscope 2 is for medical use as an example, the endoscope 2 may be for industrial use.

The endoscope 2 includes an insertion section 11, an operation section 15, and a universal cable 16.

The insertion section 11 is, for example, an elongated member to be inserted into a subject such as the body of a living organism. The insertion section 11 includes a flexible tube portion (corrugated tube) 12, a bending portion 13, and a distal end portion 14 from a proximal end side to a distal end side.

The flexible tube portion 12 is a tube portion that is provided to extend from the distal end side of the operation section 15 in an elongated manner, and has flexibility.

The bending portion 13 is provided on the distal end side of the flexible tube portion 12, and is bendable by an operation of the operation section 15. By bending the bending portion 13, a direction in which the distal end portion 14 is directed, that is, a direction of observation with the endoscope 2 can be changed.

The distal end portion 14 is provided on the distal end side of the bending portion 13, and includes an illumination lens (not shown) and components related to image pickup (components including an image pickup device 25) as will be explained later with reference to FIG. 2 and the like.

The operation section 15 is a part to be grasped and operated by a user, and is provided with an input device such as a bending operation knob for a bending operation of the bending portion 13 and various scope switches including a switch for performing an image pickup operation.

The universal cable 16 extends out of the operation section 15, and is configured to be connected to the light source device 3 with a connector 17.

A light guide (not shown) for transmitting illumination light generated by the light source device 3 and a signal line (not shown) connected to the image pickup device 25 are disposed in the endoscope 2 including the insertion section 11, the operation section 15, and the universal cable 16.

The light source device 3 includes a light source. Illumination light emitted from the light source enters an incident end of the light guide, and is transmitted to an emission end of the light guide positioned in the distal end portion 14 of the insertion section 11. The subject is irradiated with the illumination light emitted from the emission end of the light guide via an illumination lens.

Signal cables 18, in which signal lines to be connected to the image pickup device 25 are disposed, branch and extend out of the connector 17. Electric connectors 19 are provided for distal end portions of the signal cables 18, and the electric connectors 19 are connected to the processor 4. The signal lines connected to the image pickup device 25 are electrically connected to the processor 4 accordingly. Note that a signal line through which the processor 4 and the light source device 3 communicate with each other is also disposed in the signal cables 18. Note that a form may be adopted in which the function of the electric connectors 19 is integrally included in the connector 17 rather than separately providing the connector 17 and the electric connectors 19. In this case, by electrically connecting the light source device 3 and the processor 4 individually, the signal lines from the image pickup device 25 are electrically connected to the processor 4 via the light source device 3.

The processor 4 is assumed to be configured such that an ASIC (application specific integrated circuit) including a CPU (central processing unit) or the like, an FPGA (field programmable gate array), or the like reads and executes a processing program stored in a storage device such as a memory (or a recording medium) to carry out a function of each part. However, the processor 4 is not limited to this, and may be implemented as a dedicated electronic circuit for carrying out the function of each part, for example.

The processor 4 supplies power to the image pickup device 25, and transmits a control signal to the image pickup device 25 to cause the image pickup device 25 to perform image pickup. An image pickup signal generated by image pickup performed by the image pickup device 25 is transmitted to the processor 4 via the signal line, and is subjected to image processing, so that an image is generated. The processor 4 generates a video signal for display from the generated image, and outputs the video signal to the monitor 5. The processor 4 also controls the amount of illumination light emitted from the light source device 3 based on the generated image (or the image pickup signal acquired from the endoscope 2) such that brightness of the subject becomes proper.

The monitor 5 is a display device that receives the video signal from the processor 4, and displays an endoscope image.

The keyboard 6 is an input device connected to the processor 4 for inputting a command and data in accordance with an operation of a user to the processor 4. Note that various devices such as a mouse, a track ball, and a foot switch may further be provided as the input device.

Figure 2:
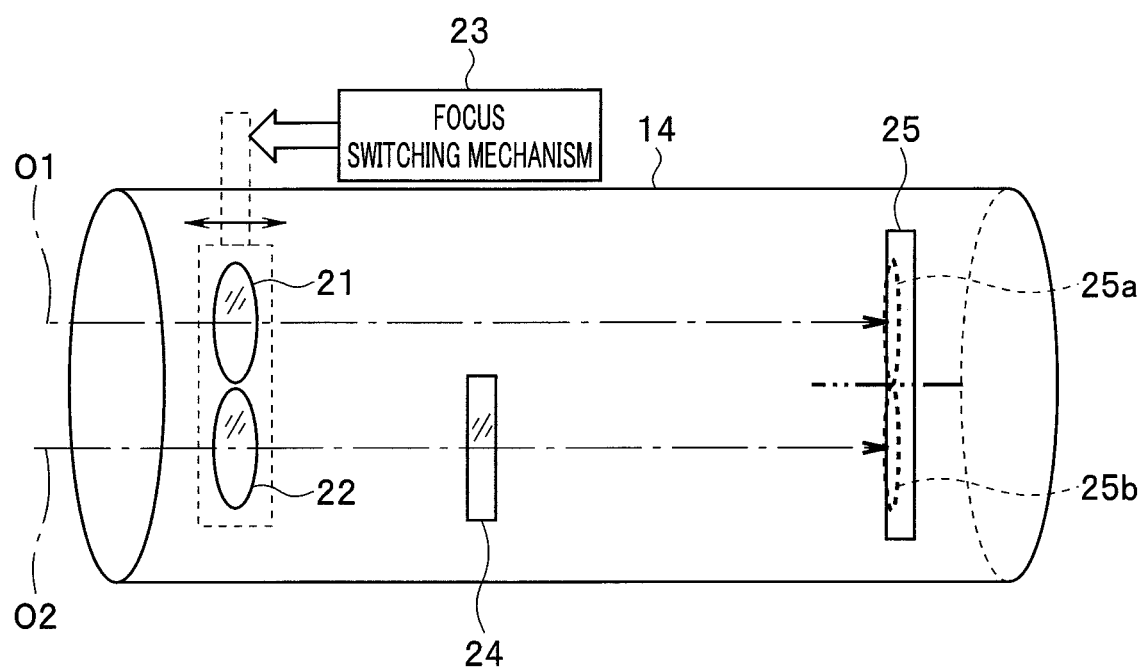
FIG. 2 is a diagram showing a principal part of components related to image pickup at a distal end portion of an insertion section of an endoscope according to the above-described first embodiment.

Next, FIG. 2 is a diagram showing a principal part of components related to image pickup at the distal end portion 14 of the insertion section 11 of the endoscope 2.

The distal end portion 14 of the insertion section 11 is provided with a first optical lens 21, a second optical lens 22, an optical path length changing filter 24, and the image pickup device 25.

The first optical lens 21 forms a first optical image of the subject.

The second optical lens 22 is provided separately from the first optical lens 21, and forms a second optical image of the subject with parallax relative to the first optical image.

Herein, the first optical lens 21 and the second optical lens 22 are configured by combining one or more lenses and an optical aperture, for example. Optical lenses of the same design are preferably used for the first optical lens 21 and the second optical lens 22 such that the first optical image and the second optical image conform with each other in a case in which the optical path length changing filter 24 is not present on an optical path.

The first optical lens 21 and the second optical lens 22 are arranged in parallel at an angle of convergence such that horizontal binocular parallax when an endoscope image is displayed occurs, for example. A second optical axis O2 of the second optical lens 22 is an optical axis different from a first optical axis O1 of the first optical lens 21. Such a horizontal arrangement is suitable for a stereoscopic observation mode which will be explained later in a third embodiment.

Note that for obtaining an extended depth-of-focus image, the first optical lens 21 and the second optical lens 22 preferably have smaller parallax. For this reason, particularly for an endoscope of a type for observing tissues of a digestive organ at a very proximate position, for example, the first optical axis O1 of the first optical lens 21 and the second optical axis O2 of the second optical lens 22 may be designed to be located as proximate as possible in order to minimize the influence of the angle of convergence.

The optical path length changing filter 24 is an optical path length changing member that makes an optical path length of the first optical image and an optical path length of the second optical image different. The optical path length changing filter 24 is provided in an optical path between the second optical lens 22 and the image pickup device 25, for example.

Note that although the example of providing the optical path length changing filter 24 in an optical path between the second optical lens 22 and the image pickup device 25 is shown herein, it goes without saying that the optical path length changing filter 24 may alternatively be provided in an optical path between the first optical lens 21 and the image pickup device 25.

Specific examples of the optical path length changing filter 24 include an optical filter formed of a transparent optical material (such as glass or optical plastic) having a refractive index larger than refractive indexes of the first optical lens 21 and the second optical lens 22 so as to have a thickness in accordance with an optical path length to be changed.

With such a configuration, the optical path length changing filter 24 transmits the second optical image so as to make the optical path length between the second optical lens 22 and the image pickup device 25 different from an actual distance between the second optical lens 22 and the image pickup device 25.

By providing the optical path length changing filter 24 in this manner, the first optical image and the second optical image become images having different focuses (being in focus at different positions).

The image pickup device 25 performs image pickup of the first optical image formed by the first optical lens 21 to generate a first image pickup signal, and performs image pickup of the second optical image formed by the second optical lens 22 to generate a second image pickup signal.

The image pickup device 25 performs image pickup of the first optical image at one portion 25a of a single image pickup plane, and performs image pickup of the second optical image at another portion 25b of the image pickup plane, for example.

However, the image pickup device 25 is not limited to the configuration, but may be composed of two image pickup devices divided at a portion indicated by a dashed-and-double-dotted line. In other words, the image pickup device 25 may have a configuration in which a first image pickup device that performs image pickup of the first optical image and the second image pickup device that performs image pickup of a second optical image are arranged in parallel.

In the case of configuring the image pickup device 25 by the first image pickup device and the second image pickup device which are separate devices, a member other than the optical path length changing filter 24 may be employed as the optical path length changing member. For example, a stepped fixing member (an image pickup device holding member) may be used as the optical path length changing member to fix the first image pickup device on a first step of the fixing member and the second image pickup device on a second step of the fixing member, thereby making a distance from the first optical lens 21 to the first image pickup device along the first optical axis O1 and a distance from the second optical lens 22 to the second image pickup device along the second optical axis O2 different, and furthermore, making optical path lengths different.

Further as shown in FIG. 2, a focus switching mechanism 23 that switches a focusing position of the first optical lens 21 and a focusing position of the second optical lens 22 to at least two of a near point and a far point may be provided. Employment of such a configuration enables an extended depth-of-focus image at the near point (in a case of observing the subject in a closely proximate state) and an extended depth-of-focus image at the far point (in a case of observing subject tissues at a distance) to be switched and observed.

Figure 3:
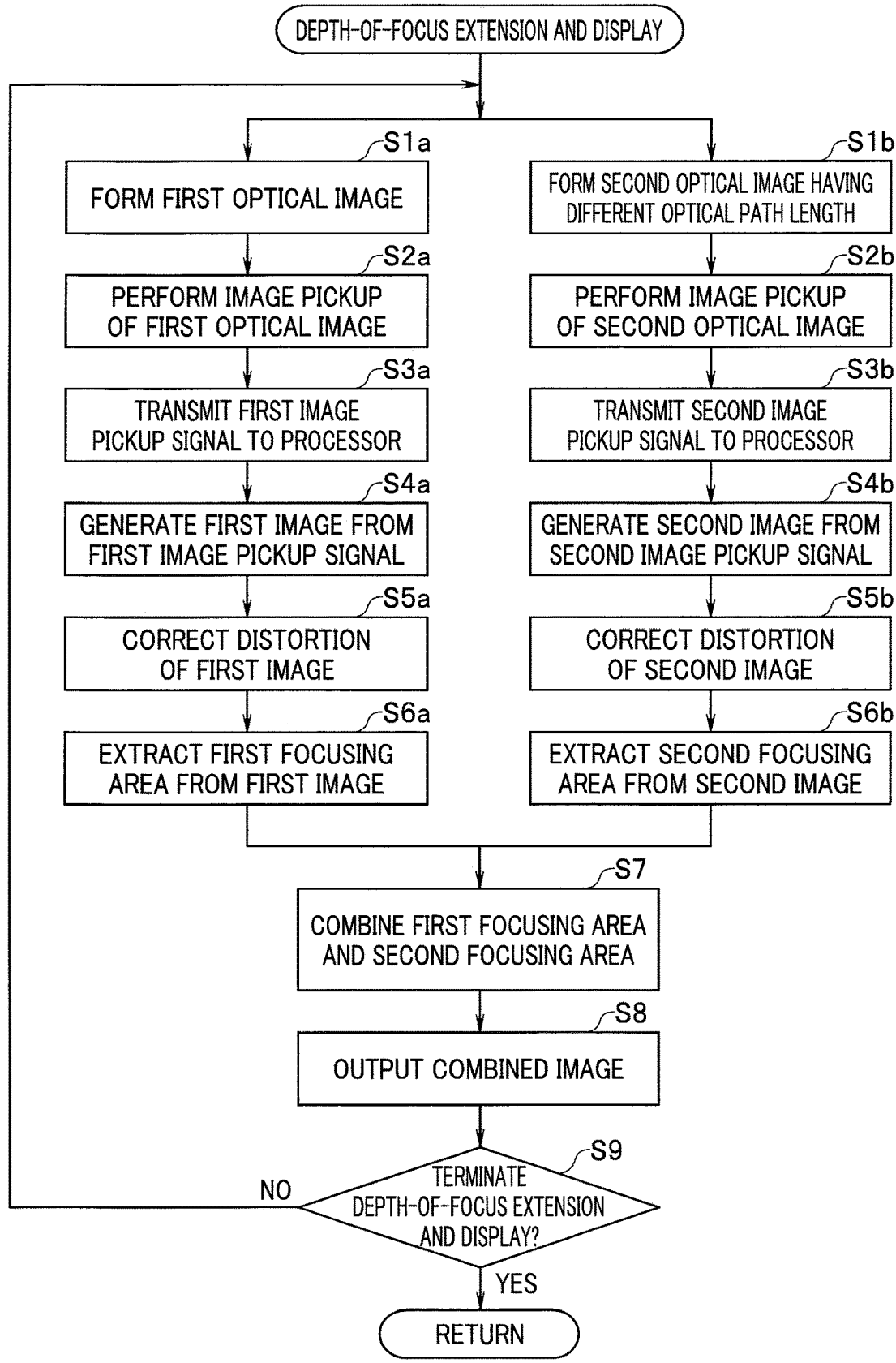
FIG. 3 is a flowchart showing depth-of-focus extension and display processing in the endoscope apparatus of the above-described first embodiment.

FIG. 3 is a flowchart showing depth-of-focus extension and display processing in the endoscope apparatus 1.

In main processing (not shown) in the endoscope apparatus 1, when, for example, an operation of selecting a depth-of-focus extension and display mode is performed with the keyboard 6, the input device of the operation section 15, or the like, the depth-of-focus extension and display processing is started.

Then, the first optical image of the subject is formed by the first optical lens 21 (step S1a), and the second optical image of the subject having a different optical path length from the optical path length of the first optical image is formed by the second optical lens 22 (step S1b).

Then, image pickup of the first optical image is performed at the one portion 25a of the image pickup plane of the image pickup device 25 to generate the first image pickup signal (step S2a), and image pickup of the second optical image is performed at the other portion 25b of the image pickup plane to generate the second image pickup signal (step S2b).

Herein, for example, the image pickup device 25 is assumed to concurrently perform image pickup of the first optical image and image pickup of the second optical image to generate the first image pickup signal and the second image pickup signal. However, the image pickup device 25 is not limited thereto, but may alternately perform image pickup of the first optical image and image pickup of the second optical image (hence, make an image pickup start time and an image pickup termination time of the first optical image different from an image pickup start time and an image pickup termination time of the second optical image) to alternately generate the first image pickup signal and the second image pickup signal.

The image pickup device 25 transmits, via the signal line, the first image pickup signal to the processor 4 (step S3a), and transmits the second image pickup signal to the processor 4 (step S3b).

The processor 4 generates the first image and the second image based on the first image pickup signal and the second image pickup signal generated by concurrent image pickup (or consecutive image pickup in alternate image pickup) (steps S4a and S4b).

Figure 4:
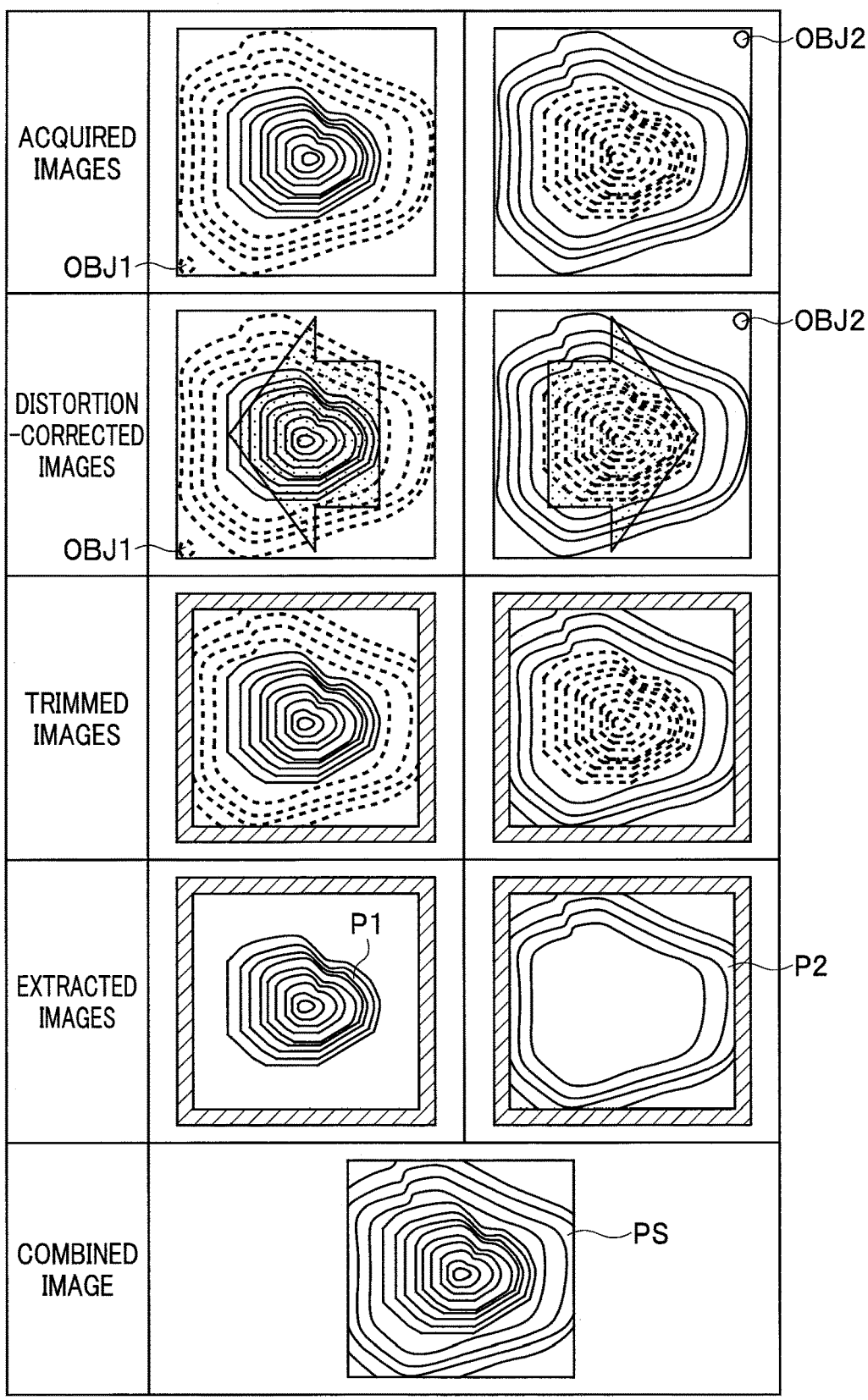
FIG. 4 is a chart for explaining a procedure of generating a combined image from a first image and a second image in the above-described first embodiment.
Figure 5:
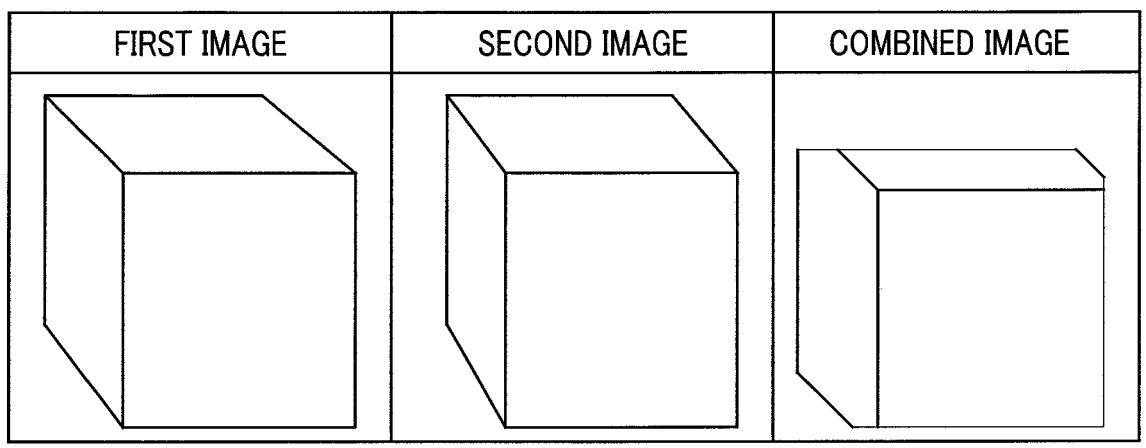
FIG. 5 is a chart for explaining a way of generating a combined image from a common portion of a first image and a second image having parallax in the above-described first embodiment.

Herein, FIG. 4 is a chart for explaining a procedure of generating a combined image from a first image and a second image, and FIG. 5 is a chart for explaining a way of generating a combined image from a common portion of a first image and a second image having parallax.

The first image generated from the first image pickup signal is assumed to be an image shown on the left side of an acquired image column in FIG. 4, and the second image generated from the second image pickup signal is assumed to be an image shown on the right side of the acquired image column in FIG. 4.

One of the first image and the second image generated from the first optical image and the second optical image having binocular parallax is a right-eye image obtained by looking at the subject from the right side, and the other is a left-eye image obtained by looking at the subject from the left side. In this case, coordinates on the first image and coordinates on the second image of a specific position (for example, a position at the back of a lumen) of the subject are typically different. Further, since a distance from the first optical lens 21 to any position of the subject and a distance from the second optical lens 22 to the same position are different, the first image and the second image are different in perspective. The first image and the second image do not conform with each other accordingly even if the first image and the second image are overlapped.

Therefore, the processor 4 subjects at least one of the first image or the second image to image processing of correcting the parallax.

First, the processor 4 performs processing of correcting a distortion of at least one of the first image or the second image as the image processing of correcting the parallax. In the present embodiment, processing of correcting a distortion caused by the angle of convergence is performed on the first image (step S5a) and on the second image (step S5b).

More specifically, it is assumed that the first image shown on the left side of the acquired image column in FIG. 4 is the right-eye image, and the second image shown on the right side is the left-eye image. It is further assumed that the first optical axis O1 and the second optical axis O2 are parallel, and the back of the lumen of the subject is intermediately located between the first optical axis O1 and the second optical axis O2.

In this case, the back of the lumen is positioned on the right side of the whole lumen in the right-eye image, and positioned on the left side of the whole lumen in the left-eye image. Further, when considering a square object plane vertical to the first optical axis O1 and the second optical axis O2, the object plane appears in a trapezoidal shape with the left side reduced by a perspective in the right-eye image, and the object plane appears in a trapezoidal shape with the right side reduced by the perspective in the left-eye image.

Consequently, the processor 4 performs shift correction such that a central partial area of the first image is shifted leftward, and a central partial area of the second image is shifted rightward in order that a portion (for example, the back of the lumen of the subject) intermediately located between the first optical axis O1 and the second optical axis O2 is positioned at the center of the image. In this shift correction, other partial areas are also shifted in accordance with coordinates.

The processor 4 also performs distortion correction such as trapezoid correction on the first image and the second image such that a distortion caused by the perspective is corrected (see a distortion-corrected image column in FIG. 4).

Further, a subject OBJ1 appearing at the lower left in the first image shown on the left side of the acquired image column in FIG. 4 does not appear in the second image shown on the right side of the acquired image column in FIG. 4, and a subject OBJ2 appearing at the upper right in the second image shown on the right side of the acquired image column in FIG. 4 does not appear in the first image shown on the left side of the acquired image column in FIG. 4.

Thus, the processor 4 performs processing (trimming processing) of removing an area including a figure present only in one of the first image and the second image. Note that the trimming processing may be performed as processing of extracting areas including a common figure from the first image and the second image, respectively. Hatched areas in a trimmed image column in FIG. 4 indicate the areas removed by the trimming processing.

In a case of alternately performing image pickup of the first optical image and image pickup of the second optical image as described above, the processor 4 may further perform processing of correcting a positional displacement between the first image and the second image resulting from a difference in image pickup time point.

In addition, the processor 4 may perform other types of processing for matching the first image and the second image, such as correction of aberrations (including various aberrations such as a barrel or spool distortion aberration, a spherical aberration, and a chromatic aberration) of the optical lenses and correction of a difference in magnification.

Then, the processor 4 extracts a first focusing area P1 from the first image (step S6a), and extracts a second focusing area P2 from the second image (step S6b) (see an extracted image column in FIG. 4).

Figure 6:
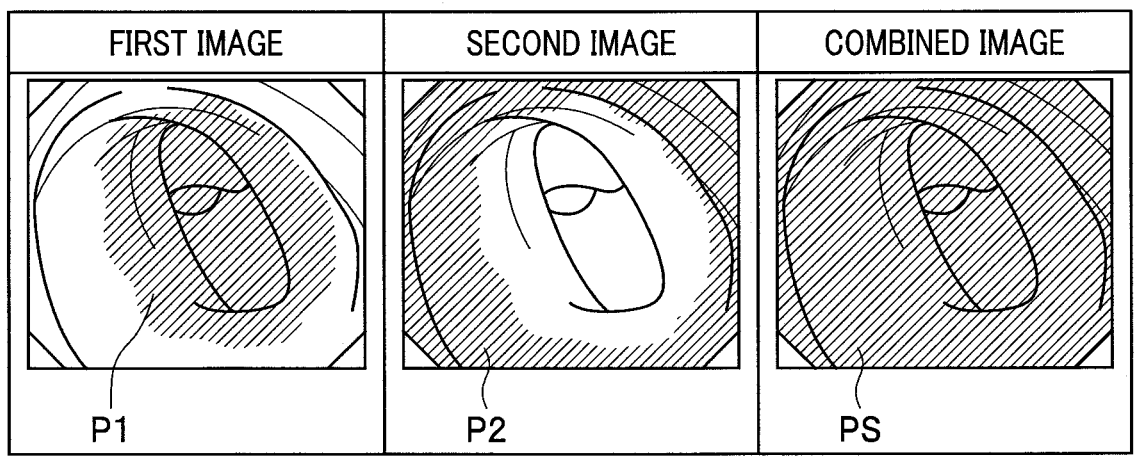
FIG. 6 is a chart showing a first focusing area extracted from the first image and a second focusing area extracted from the second image, and a combined focusing area of the combined image in the above-described first embodiment.

Herein, FIG. 6 is a chart showing the first focusing area P1 extracted from the first image and the second focusing area P2 extracted from the second image, as well as a combined focusing area PS of a combined image.

More specifically, with respect to the area including the figure common to the first image and the second image, the processor 4 causes an area in the first image having contrast higher than contrast of an area in the second image to be included in the first focusing area P1, causes an area in the second image having contrast higher than contrast of an area in the first image to be included in the second focusing area P2, cuts out the first focusing area P1 from the first image, and cuts out the second focusing area P2 from the second image.

Then, the processor 4 combines the first focusing area P1 and the second focusing area P2 to generate an endoscope image which is a combined image (step S7). FIG. 5 shows a way in which the combined image is generated from a common portion (for example, a portion in which the shape of the subject is the same within a predetermined allowable range in the first image and the second image) of the first image and the second image having parallax.

When generating the combined image, boundary processing of aligning and positioning portions roughly matched in contour and de-emphasizing the boundary (processing of filling pixels little by little from adjacent portions) may be performed. On this occasion, adjacent areas may be matched in hue and brightness.

The endoscope image thus generated is converted by the processor 4 into a video signal and outputted to be displayed on the monitor 5 (step S8).

The endoscope image displayed on the monitor 5 is an extended depth-of-focus image (for example, an image in focus both on the far side (back side) and the proximal side of the lumen) having the combined focusing area PS including the first focusing area P1 in the first image and the second focusing area P2 in the second image as shown in FIG. 6.

Thereafter, the processor 4 determines whether an operation of terminating the depth-of-focus extension and display mode has been performed (step S9). In a case of determining that the operation has not been performed, the processor 4 returns to steps S1a and S1b described above to perform the processing as described above. In a case of determining that the operation has been performed, the processor 4 leaves the processing to return to the main processing (not shown).

According to the first embodiment, optical images are formed by the first and second optical lenses 21 and 22 separately configured, respectively, and the parallax between the first image and the second image obtained by performing image pickup of the respective optical images by the image pickup device 25 is corrected to combine an endoscope image. This enables an extended depth-of-focus image to be observed. At this time, a beam splitter in which a plurality of prisms are combined is not required, which provides advantages that the distal end portion 14 of the insertion section 11 of the endoscope 2 can be prevented from increasing in weight and insertion performance of the endoscope 2 is less impaired.

The use of the optical path length changing filter 24 as the optical path length changing member enables the optical path length of the first optical image and the optical path length of the second optical image to be different in a desired manner merely by adjusting the refractive index and the thickness of the optical path length changing filter 24. This enables the first optical lens 21 and the second optical lens 22 to have the same design, and further enables the first optical image and the second optical image to be formed on the same image pickup plane of the image pickup device 25.

Since the first image and the second image are combined after removing the area including the figure present only in one of the first image and the second image, an unnatural feeling when images having parallax are combined can be reduced.

Further, since with respect to the area including the figure common to the first image and the second image, areas having higher contrast are combined to generate an endoscope image, an endoscope image having an appropriately extended depth of focus can be obtained.

In addition, since a distortion of at least one of the first image or the second image is corrected, mismatch when combining the first image and the second image can be reduced to obtain a more natural endoscope image.

In particular, by performing the processing of correcting a distortion caused by the angle of convergence on the first image and the second image, an endoscope image that gives little unnatural feeling, close to an extended depth-of-focus image acquired using a single optical lens and a beam splitter can be obtained.

Since the first image pickup signal and the second image pickup signal generated by concurrent image pickup are processed to generate an endoscope image, a high-integrity endoscope image can be generated based on the first image and the second image with no blur even if relative positions of the distal end portion 14 and the subject are changed with the lapse of time.

On the other hand, in the case of alternately performing pickup of the first optical image and pickup of the second optical image, a relatively high-integrity endoscope image can be generated based on the first image and the second image having reduced blurs by processing the first image pickup signal and the second image pickup signal generated by consecutive image pickup (that is, image pickup with a small temporal difference) to generate an endoscope image.

In a case of performing image pickup of the first optical image at a portion of the single image pickup plane provided for the image pickup device 25 and performing image pickup of the second optical image at another portion, an extended depth-of-focus image can be obtained merely by providing the single image pickup device 25, which can achieve cost reduction.

In the case of providing the first image pickup device that performs image pickup of the first optical image and the second image pickup device that performs image pickup of the second optical image, the frame rate can be improved by driving the two image pickup devices in parallel.

Further, by providing the focus switching mechanism 23 that switches the focusing position of the first optical lens 21 and the focusing position of the second optical lens 22 to at least two of the near point and the far point, an extended depth-of-focus image at the near point and an extended depth-of-focus image at the far point can be switched and observed.

Thus, even in a case in which the distal end portion 14 of the endoscope 2 approaches a subject having a depth, the subject can be observed as a whole in a focusing state while eliminating the need for switching focuses and eliminating focus fine adjustment. This enables a lesion having a depth, for example, to be clearly observed as a whole, and a diagnosis to be performed immediately without requiring the labor such as moving the endoscope 2 close to the subject or away from the subject.

Second Embodiment

Figure 7:
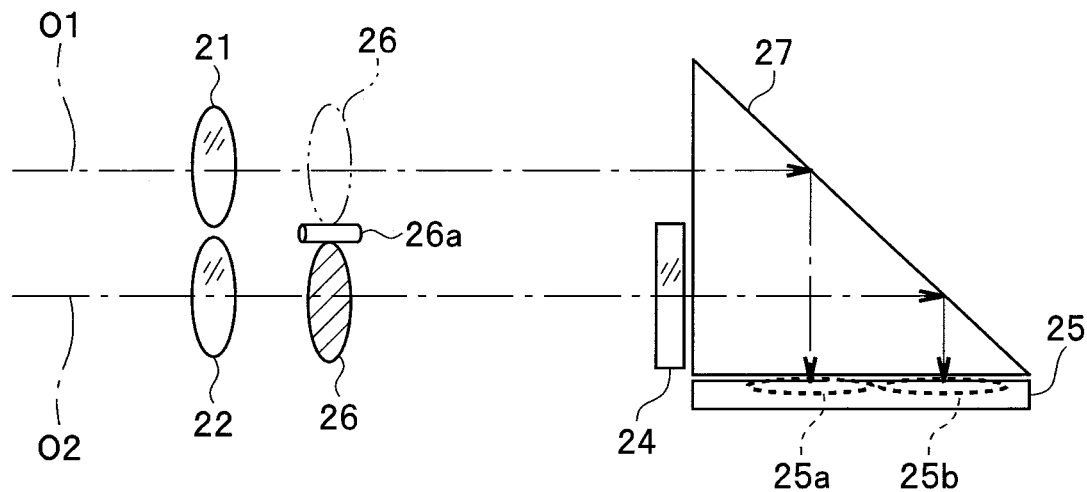
FIG. 7 is a diagram showing a principal part of components related to image pickup at a distal end portion of an insertion section of an endoscope according to a second embodiment of the present invention.

FIG. 7 shows a second embodiment of the present invention, and is a diagram showing a principal part of components related to image pickup at the distal end portion 14 of the insertion section 11 of the endoscope 2.

In the second embodiment, portions similar to portions of the above-described first embodiment are denoted the same reference characters and explanation is omitted as appropriate, and different points will mainly be explained.

In the present embodiment, a prism 27 as a reflecting optical system is further provided as a component related to image pickup at the distal end portion 14.

The image pickup device 25 is provided such that the image pickup plane is vertical to the first optical axis O1 and the second optical axis O2 in the above-described first embodiment. In contrast, the image pickup device 25 of the present embodiment is arranged such that the image pickup plane is parallel to the first optical axis O1 and the second optical axis O2, for example.

The prism 27 reflects the first optical image from the first optical lens 21 and the second optical image from the second optical lens 22 to the image pickup device 25.

Note that the image pickup device 25 performs image pickup of the first optical image at the one portion 25a of the image pickup plane, and performs image pickup of the second optical image at the other portion 25b of the image pickup plane, similarly to the above-described first embodiment.

In addition, the image pickup device 25 may be composed of two image pickup devices, and the focus switching mechanism 23 that switches the focusing positions may further be provided, similarly to the above-described first embodiment.

Further, the image pickup device 25 may perform image pickup of the first optical image and image pickup of the second optical image concurrently or alternately, similarly to the above description in the first embodiment.

In the case of alternately performing image pickup, for example, a shutter 26 that controls passage/light shielding of the first optical image and passage/light shielding of the second optical image may further be provided.

The shutter 26 in the configuration example shown in FIG. 7 includes a light shielding member configured to rotate about a rotation shaft 26a, for example, and is configured such that the first optical image is shielded and the second optical image is passed when the light shielding member is located on the first optical axis O1, and the second optical image is shielded and the first optical image is passed when the light shielding member is located on the second optical axis O2.

Alternate image pickup of the first optical image and the second optical image as explained in the above-described first embodiment may be performed using the shutter 26 of such a configuration.

However, the use of the shutter 26 is not a limitation, and electronic shutters may be independently applied to the one portion 25a of the image pickup plane and the other portion 25b of the image pickup plane to close the electronic shutter for the other portion 25b of the image pickup plane (for example, reset a photodiode) when the electronic shutter for the one portion 25a of the image pickup plane is opened (more specifically, charges are being accumulated in the photodiode), and to open the electronic shutter for the other portion 25b of the image pickup plane when the electronic shutter for the one portion 25a of the image pickup plane is closed, thereby alternately performing image pickup of the first optical image and the second optical image.

Further, the one portion 25a of the image pickup plane and the other portion 25b of the image pickup plane may be configured as different pixel groups, and reading from the pixel group of the other portion 25b may be performed when image pickup is performed with the pixel group of the one portion 25a, and reading from the pixel group of the one portion 25a may be performed when image pickup is performed with the pixel group of the other portion 25b.

The second embodiment exerts effects substantially similar to the effects of the above-described first embodiment, and even if the single prism 27 is provided, an extended depth-of-focus image can be obtained while achieving weight reduction as compared with the case of combining a plurality of prisms.

Since the optical path can be bent by the prism 27, the flexibility in layout of the image pickup device 25 can be increased, and a design suitable for the model of the endoscope 2 (to cite an example, a side-viewing endoscope) can be performed.

Third Embodiment

Figure 8:
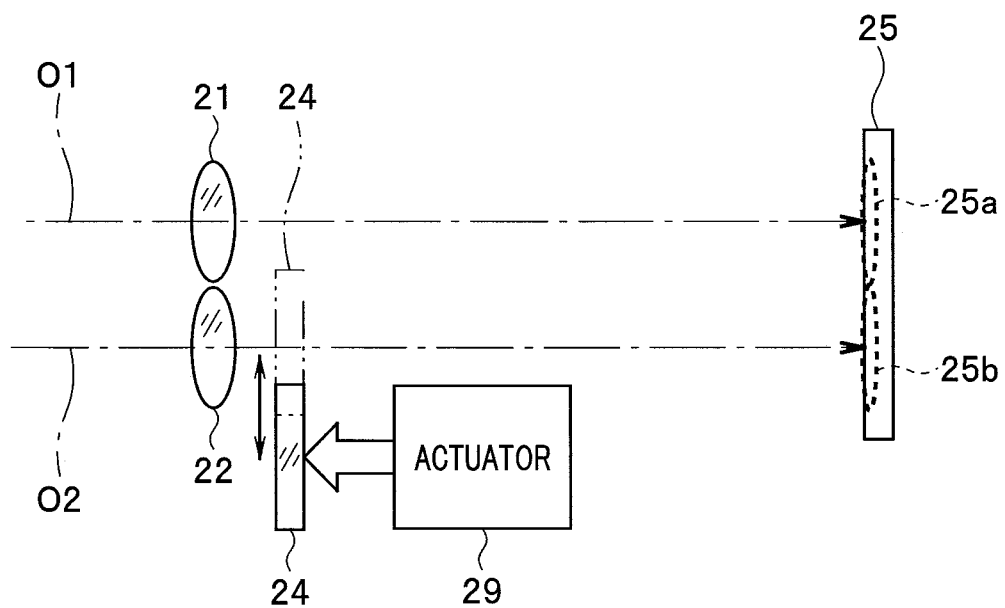
FIG. 8 is a diagram showing a principal part of components related to image pickup at a distal end portion of an insertion section of an endoscope according to a third embodiment of the present invention.

FIG. 8 shows a third embodiment of the present invention, and is a diagram showing a principal part of components related to image pickup at the distal end portion 14 of the insertion section 11 of the endoscope 2.

In the third embodiment, portions similar to portions of the above-described first and second embodiments are denoted the same reference characters and explanation is omitted as appropriate, and different points will mainly be explained.

In the configuration of the first embodiment shown in FIG. 2, the optical path length changing filter 24 is provided fixedly in the optical path between the second optical lens 22 (or the first optical lens 21) and the image pickup device 25. However, the present embodiment is configured such that the optical path length changing filter 24 can be inserted/withdrawn from above the optical path.

In other words, the present embodiment further includes, as a component related to image pickup at the distal end portion 14, an actuator 29 as a driving mechanism that inserts/withdraws the optical path length changing filter 24 into/from the optical path between the second optical lens 22 and the image pickup device 25 (which may be the optical path between the first optical lens 21 and the image pickup device 25; the same applies hereinafter). The actuator 29 inserts the optical path length changing filter 24 into the optical path or withdraws the optical path length changing filter 24 from the optical path based on control of the processor 4.

In such a configuration, in the case in which the depth-of-focus extension and display mode which is a first mode is selected, the processor 4 controls the actuator 29 to insert the optical path length changing filter 24 into the optical path between the second optical lens 22 and the image pickup device 25.

Then, similarly to the above-described first and second embodiments, the processor 4 processes the first image pickup signal generated by performing image pickup of the first optical image and the second image pickup signal generated by performing image pickup of the second optical image formed with the optical path length different from the optical path length of the first optical image, thereby generating an extended depth-of-focus endoscope image.

In a case in which a stereoscopic observation mode (3D mode) which is a second mode is selected, the processor 4 controls the actuator 29 to withdraw the optical path length changing filter 24 from the optical path between the second optical lens 22 and the image pickup device 25.

Then, the processor 4 processes the first image pickup signal generated by performing image pickup of the first optical image and the second image pickup signal generated by performing image pickup of the second optical image formed with the optical path length identical to the optical path length of the first optical image, thereby generating the first image and the second image.

At this time, the processor 4 generates a 3D endoscope image for stereoscopic vision utilizing the parallax without performing the processing of correcting the parallax between the first image and the second image. The 3D endoscope image thus generated is displayed on the monitor 5 corresponding to stereoscopic display.

Note that also in the configuration of the present embodiment, the image pickup device 25 may concurrently or alternately perform image pickup of the first optical image and image pickup of the second optical image. Further, it goes without saying that the prism 27 as the reflecting optical system as explained in the above-described second embodiment may be provided for the configuration of the present embodiment.

Since the third embodiment exerts effects substantially similar to the effects of the above-described first and second embodiments, and the actuator 29 as the driving mechanism that inserts/withdraws the optical path length changing filter 24 into/from the optical path is further provided, a 3D endoscope image utilizing the parallax can be generated when the optical path length changing filter 24 is withdrawn from the optical path.

In this manner, the endoscope apparatus 1 having multiple functions that enables an extended depth-of-focus endoscope image and a 3D endoscope image to be switched and observed.

Note that although the case in which the present invention is an endoscope apparatus has been mainly explained above, the present invention is not limited thereto, but may be a method for generating an endoscope image by a method similar to a method of the endoscope apparatus, a computer program for causing a computer to perform processing similar to processing of the endoscope apparatus, a computer-readable non-transitory recording medium having the computer program recorded on the recording medium, or the like.

The present invention is not limited to the embodiments as described above, but can be embodied with constitutional elements modified within a range not deviating from the gist in an implementation phase. In addition, various aspects of the invention can be formed by appropriate combinations of a plurality of constitutional elements disclosed in the above-described embodiments. For example, some constitutional elements may be removed from all the constitutional elements shown in the embodiments. Further, constitutional elements in different embodiments may be combined as appropriate. In this manner, it is obviously possible to make various modifications and applications within the range not deviating from the gist of the invention.

What is claimed is:

1. An endoscope apparatus comprising:
a first optical lens;
a second optical lens;
at least one image pickup device configured to generate:
a first image pickup signal based on a first optical image formed on the at least one image pickup device from the first optical lens, and
a second image pickup signal based on a second optical image formed on the at least one image pickup device from the second optical lens, wherein a first effective optical path length between the first optical lens and the at least one image pickup device is different than a second effective optical path length between the second optical lens and the at least one image pickup device; and
a processor comprising hardware, the processor being configured to:
generate a first image of an object based on the first image pickup signal, the first image having a first focused area of the object due to the first effective optical path length;
generate a second image of an object based on the second image pickup signal, the second image having a second focused area of the object due to the second effective optical path length;
correct a parallax in at least one of the first image or the second image;
determine an area in the first image having a contrast higher than a contrast of an area in the second image to be included in the first focused area to extract only the first focused area from the first image;
determine an area in the second image having a contrast higher than a contrast of an area in the first image to be included in the second focused area to extract only the second focused area from the second image; and
combine the first focused area and the second focused area to generate an endoscope image different from each of the first image and the second image.

2. The endoscope apparatus according to claim 1, further comprising an optical path length changing member provided one of in a first optical path of the first optical lens or in a second optical path of the second optical lens such that the first effective optical path length is different from the second effective optical path length.

3. The endoscope apparatus according to claim 2, wherein the optical path length changing member comprises a filter;
the first optical lens and the second optical lens are arranged with an angle of convergence such that horizontal binocular parallax when the endoscope image is displayed occurs; and
the processor is configured to:
when the filter is not provided in the first optical path and the second optical path, process the first image pickup signal and the second image pickup signal to generate a 3D endoscope image for stereoscopic vision.

4. The endoscope apparatus according to claim 3, the endoscope apparatus further comprising a driving mechanism configured to move the filter into or from one of the first optical path or the second optical path.

5. The endoscope apparatus according to claim 2, wherein
the optical path length changing member comprises a filter; and
the filter is provided in an optical path of the second optical lens, the filter is configured to transmit the second optical image such that the second effective optical path length between the second optical lens and the at least one image pickup device is greater than a distance between the second optical lens and the at least one image pickup device.

6. The endoscope apparatus according to claim 1, wherein the correcting of the parallax of at least one of the first image or the second image comprises correcting a distortion of at least one of the first image or the second image.

7. The endoscope apparatus according to claim 6, wherein
the first optical lens and the second optical lens are arranged with an angle of convergence such that horizontal binocular parallax when the endoscope image is displayed occurs, and
the processor is configured to correct the distortion caused by the angle of convergence on the first image and the second image.

8. The endoscope apparatus according to claim 1, wherein
the at least one image pickup device is configured to concurrently perform image pickup of the first optical image and image pickup of the second optical image to generate the first image pickup signal and the second image pickup signal, and
the processor is configured to simultaneously process the first image pickup signal and the second image pickup signal generated by concurrent image pickup to generate the endoscope image.

9. The endoscope apparatus according to claim 1, wherein
the at least one image pickup device is configured to alternately perform image pickup of the first optical image and image pickup of the second optical image to alternately generate the first image pickup signal and the second image pickup signal, and
the processor is configured to process the first image pickup signal and the second image pickup signal generated by consecutive image pickup to generate the endoscope image.

10. The endoscope apparatus according to claim 1, wherein the at least one image pickup device is configured to:
perform image pickup of the first optical image at a portion of a single image pickup plane, and
perform image pickup of the second optical image at another portion of the image pickup plane.

11. The endoscope apparatus according to claim 1, wherein the at least one image pickup device includes:
a first image pickup device configured to perform image pickup of the first optical image, and
a second image pickup device configured to perform image pickup of the second optical image.

12. The endoscope apparatus according to claim 1, further comprising:
a focus switching mechanism configured to switch a focusing position of the first optical lens and a focusing position of the second optical lens to at least two of a near point and a far point.

13. The endoscope apparatus according to claim 1, further comprising a prism configured to reflect a first optical image from the first optical lens and a second optical image from the second optical lens to the at least one image pickup device.

14. The endoscope apparatus according to claim 1, wherein the processor is configured to:
determine a position to match in contour of the first focusing area and the second focusing area, and
boundary processing of aligning the combined image to de-emphasize the boundary.

15. The endoscope apparatus according to claim 1, wherein the processor is further configured to:
trim the first image to exclude a first area that is not included in the second image from the first image, and
trim the second image to exclude a second area that is not included in the first image from the second image.

16. The endoscope apparatus according to claim 1, wherein the combining of the first focused area and the second focused area is conducted subsequent to the extracting of the first and second focusing area.

17. A processor comprising hardware, the processor being configured to:
acquire a first image pickup signal and a second image pickup signal from an endoscope;
generate a first image of an object based on the first image pickup signal, the first image having a first focused area of the object due to a first effective optical path length between a first optical lens and the at least one image pickup device;
generate a second image of an object based on the second image pickup signal, the second image having a second focused area of the object due to a second effective optical path length between a second optical lens and the at least one image pickup device;
correct a parallax in at least one of the first image or the second image;
determine an area in the first image having a contrast higher than a contrast of an area in the second image to be included in the first focused area to extract only the first focused area from the first image;
determine an area in the second image having a contrast higher than a contrast of an area in the first image to be included in the second focused area to extract only the second focused area from the second image; and
combine the first focused area and the second focused area to generate an endoscope image different from each of the first image and the second image.

18. The endoscope apparatus according to claim 17, wherein the first image and the second image are acquired at a same time.

19. A method for generating an endoscope image, the method comprising:
acquiring a first image;
acquiring a second image;
generating a first image of an object based on the first image pickup signal, the first image having a first focused area of the object due to a first effective optical path length between a first optical lens and the at least one image pickup device;
generating a second image of an object based on the second image pickup signal, the second image having a second focused area of the object due to a second effective optical path length between a second optical lens and the least one image pickup device;
correcting the parallax in at least one of the first image or the second image;
determining an area in the first image having a contrast higher than a contrast of an area in the second image to be included in the first focused area to extracting only the first focused area from the first image, determining an area in the second image having a contrast higher than a contrast of an area in the first image to be included in the second focused area to extracting only the second focused area from the second image, and
combining the first focused area and the second focused area to generate the endoscope image different from each of the first image and the second image.

\* \* \* \* \*